US006288110B1

(12) United States Patent
Marikovsky (10) Patent No.: US 6,288,110 B1
(45) Date of Patent: Sep. 11, 2001

(54) PHARMACEUTICAL COMPOSITIONS COMPRISING DISULFIRAM

(75) Inventor: Moshe Marikovsky, Mazkeret Batya (IL)

(73) Assignee: Yeda Research and Development Co Ltd., Rehovot (IL)

(*) Notice: Subject to any disclaimer, the term of this patent is extended or adjusted under 35 U.S.C. 154(b) by 0 days.

(21) Appl. No.: 09/582,995

(22) PCT Filed: Jan. 11, 1999

(86) PCT No.: PCT/IL99/00017
§ 371 Date: Jul. 10, 2000
§ 102(e) Date: Jul. 10, 2000

(87) PCT Pub. No.: WO99/34784
PCT Pub. Date: Jul. 15, 1999

(30) Foreign Application Priority Data

Jan. 11, 1998 (IL) .......................................... 122892

(51) Int. Cl.⁷ .......................... A01N 47/10; A61K 31/27; A61K 31/16

(52) U.S. Cl. .......................... 514/483; 514/599; 514/707; 514/866; 514/913; 514/929

(58) Field of Search .................................. 514/483, 599, 514/707, 929, 866, 913

(56) References Cited

FOREIGN PATENT DOCUMENTS 0 284 879   10/1988   (EP) .
95 30415    11/1995   (WO) .

OTHER PUBLICATIONS

Wattenberg et al., "Inhibition of 1,2–Dimethylhydrazine–Induced Neoplasia of the Large Intestine in Female CF, Mice by Carbon Disulfide: Brief Communication", *J Natl. Cancer*, vol.60, No.6, pp.1515–1517, (1978).
Verma et al., "A Randomized Phase II Study of Cisplatin Alone Versus Cisplatin Plus Dislufiram", *Am. J. Clin. Oncol*, vol.13, No.2, pp.119–124, (1990).
Valeriote et al., "Potentiation of Nitrogen Mustard Cytotoxicity by Disulfiram, Diethyldithiocarbamic Acid, and Diethylamine in Mice", *Cancer Research*, vol.49, pp.6658–6661, (1989).
Schmähl et al., "Influence of Disulfiram on the Organotropy of the Carcinogenic Effect of Dimethylnitrosamine and Diethylnitrosamine in Rats", *Z Krebsforsch*, vol.85, pp.271–276, (1976).
Rotstein et al., "Effect of exogenous glutathione on tumor progression in the murine skin multistage carcinogenesis model", *Carcinogensis*, vol.9, No.9, pp.1547–1551, (1988).
Ramesha et al., "Modulation of 7, 12–Dimethylbenz[a]anthracene–induced Transmammary Carcinogenesis by Disulfiram and Butylated Hydroxyanisole in Mice", *Jpn. J. Cancer Res.*, vol.80, pp.1171–1175, (1989).

Nigro et al., "Inhibition of Azoxymethane–Induced Intestinal Cancer by Disulfiram", *Cancer Letters*, vol.5, pp.91–95, (1978).
Mashiba et al., "Augmented Inhibition of Tumor Cell Proliferation in the Combined Use of Disulfiram with Ascorbic Acid and the involvement of Oxygen Free Radical", *Japan J. Exp. Med.*, vol.60, pp.209–214, (1990).
Malejka–Giganti et al., "Inhibitory Effect of Disulfiram on Rat Mammary Tumor Induction by N–2–Fluorenylacetamide", *J. Natl. Cancer Inst.*, vol.64, No.6, (1980).
Ishikawa et al., "Drug Interaction Effects on Antitumour Drugs (VIII): Prevention of Ifosfamide–Induced Urotoxicity by Disulfiram and Its Effect on Antitumour Activity and Acute Toxicity of Alkylating Agents in Mice", *Pharmacology & Toxicology*, vol.68, pp.21–25, (1991).
Irving et al., "Inhibitors of n–N–Butyl–N–(4–hydroxybutyl) nitrosamine–induced Urinary Bladder Cancer in Rats by Administration of Disulfiram in the Diet", *Cancer Research*, vol.39, pp.3040–3043, (1979).
Murphy et al., "The effect of disulfiram on the carcinogenicity of N–butyl–N–(3–carboxypropyl) nitrosamine in the rat", *Carcinogenesis*, vol.4, pp.617–620, (1983).
Hacker et al. "Effect of Disulfiram (Tetraethylthiuram Disulfide) and Diethyldithiocarbamate on the Bladder Toxicity and Antitumor Activity of Cyclophosphamide in Mice", *Cancer Research*, vol.42, pp.3390–4494, (1982).
Habs et al., "Effect of the Pretreatment with Disulfiram on the Toxicity and Antitumor Activity of 1–(2–Hydroxyethyl)–3–(2–Chloroethyl)–3–Nitrosourea in Sprague–Dawley Rats", *Cancer Letters*, vol.13, pp.63–69, (1981).
Forman et al., "Mechanism for the Potentiation of Oxygen Toxicity by Disulfiram", *The Journal of Pharmacology and Experimental Therapeutics*, vol.212, pp.452–455, (1980).
Fiala, "Investigations into the Metabolism and Mode of Action of the Colon Carcinogens 1,2–Dimethylhydrazine and Azoxymethane", *Cancer*, vol.40, pp.2436–2445, (1977).
Eneanya et al., "The Actions and Metabolic Fate of Disulfiram", *Ann. Rev. Pharmacol. Toxicol*, vol.21, pp.575–596, (1981).
Borchert et al., "Inhibition of Macromolecular Binding of Benzo[a]pyrene and Inhibitions of Neoplasia by Disulfiram in the Mouse Forestomach", *J. Natl. Cancer*, vol.57, No.1, pp.173–179, (1976).

(List continued on next page.)

Primary Examiner—Mukund J. Shah
Assistant Examiner—Tamthom N. Truong
(74) *Attorney, Agent, or Firm*—Browdy and Neimark (57) ABSTRACT

Disulfiram (tetraethylthiuram disulfide) is shown to inhibit angiogenesis and to be useful in the treatment of angiogenesis-dependent disorders, including neoplasms, and to prevent cell hyperproliferation and formation of clots along or around medical devices.

9 Claims, 7 Drawing Sheets

OTHER PUBLICATIONS

Cheever et al., "Ethylene Dichloride: The Influence of Disulfiram of Ethanol on Oncogenicity, Metabolism, and DNA Covalent Binding in Rats", *Fundamental and Applied Toxicology*, vol.14, pp.243–261, (1990).

Ishikawa et al., "Drug Interaction Effects on Antitumor Drugs (XV): Disulfiram as Protective Agent Cyclophosphamide–Induced Urotoxicity Without Compromising Antitumor Activity in Mice", *Pharmacology & Toxicology*, vol.74, pp.255–261, (1994).

M. Takaishi, "Inhibition of spontaneous leukemia in F–344 rats by tetramethylthiuram disulfide," Gann, vol. 74, No. 6, 1983, pp. 810–813.

G. Weber, "Neue systemische Therapie der Psoriasis", Hautzart, vol. 36, No. 1, 1985, pp. 20–24.

B.S. Warren, "Mechanisms of inhibition of tumor progression," Basic Life Sci., vol. 61, 1993, pp. 279–289.

G.Y. Liu, "Induction of apoptosis by thiuramdisulfides, the reactive metabolites of dithiocarbamates, through coordinative modulation of NfkB, c–fos/c–jun, and p53 proteins," Mol. Carcinogen, vol. 22, No. 4, 1988, pp. 235–246.

D.J. Stewart, "Phase I study of the combination of disulfiram with cisplatin", Am. J. Clin. Oncol., vol. 10, No. 6, 1987, pp. 517–519.

H.K.A. Schirmer, "Disulfiram and tumor inhibition," Transactions of the American Association of Genito–Urinary Surgeons, vol. 58, 1966, pp. 63–66.

G.N. Hannan, "Regulation of polypeptide synthesis in endothelial cells and hybridoma cells by the copper ionophore disulfiram," Cell Biol. Int. Rep., vol. 6, No. 5, 1982, pp. 423–432.

PHARMACEUTICAL COMPOSITIONS COMPRISING DISULFIRAM

CROSS REFERENCE TO RELATED APPLICATION

The present application is the national stage under 35 U.S.C. 371 of PCT/IL99/00017, filed Jan. 11, 1999.

FIELD OF THE INVENTION

The present invention relates to the use of disulfiram as an angiogenesis inhibitor for the preparation of pharmaceutical compositions useful for the treatment of angiogenesis-dependent disorders and to a method of treatment of said disorders.

BACKGROUND OF THE INVENTION

Bis(diethylthiocarbamoyl) disulfide or tetraethylthiuram disulfide, hereinafter disulfiram, is an inhibitor of various enzymes and a chelator of heavy metals. Disulfiram is known as an alcohol deterrent and is the active ingredient of the drug Antabuse used in aversion therapy, an adjunctive treatment for chronic alcoholism (Haley, 1979). Disulfiram has an ampiphilic nature, is soluble in water but it solubilizes better in hydrophobic solutions such as methanol, acetone or chloroform.

Once ingested and absorbed through the intestinal tract or injected intraperitoneally as a colloidal suspension, disulfiram is extensively distributed throughout the body including the brain (Faiman, 1978). It is quickly converted into its main metabolite, diethyldithiocarbamate (DDC) (Eneanya, 1981), whereby the disulfide is reduced to a sulfhydryl group. The DDC produced is then further metabolized via different ways which include a non-enzymatic degradation to diethylamine (DEA) (Brien, 1983).

Both disulfiram and DDC are potent chelators of copper, iron and zinc. Chelation of the metal portion of an enzyme by disulfiram or DDC might lead to the inactivation of such enzyme. Thus disulfiram was shown to inhibit various zinc-containing dehydrogenases, such as aldehyde dehydrogenases as well as oxidases, dopamine-β-hydroxylases and aldolases (Eneanya, 1981). Inhibition of aldehyde dehydrogenases by disulfiram inhibits glycolysis, the tricarboxylic acid cycle and the pentose phosphate shunt.

Disulfiram was shown to interfere with induction of cancer by various carcinogens, often by inhibiting their metabolic activation, as shown for bladder cancer in rats exposed to N-butyl-N-(4-hydroxybutyl)nitrosamine (Irving, 1979) or to N-butyl-N-(3-carboxypropyl)nitrosamine (Irving, 1983), for liver tumors in rats induced by dimethyl- or diethylnitrosamine (Schmahl, 1976), for intestinal cancer induced by azoxymethane in rats (Nigro, 1978) (probably by blocking the metabolism of azoxymethane), for neoplasia of the large bowel induced by 1,2-dimethylhydrazine (Wattenberg, 1978), and in neoplasia of the forestomach induced by benzo(a)pyrene in mice (Borchert, 1976). Disulfiram inhibited the metabolism of the carcinogen azomethane thus offering protection from the oxymetabolite neoplasia (Fiala, 1977). Disulfiram was also shown to inhibit tumor progression—from papilloma to squamous cell carcinoma—in the murine skin multistage carcinogenesis model (Rotstein, 1988), to inhibit transmammary carcinogenesis induced in mice by 7,12-dimethylbenz(a)anthracene (Rao, 1989) and to reduce the incidence of mammary tumors induced in rats by N-2-fluorenylacetamide or N-hydroxy-N-2-fluorenylacetamide through inhibition of their metabolic activation (Malejka Giganti, 1980). Since a cytosolic aldehyde dehydrogenase is induced during rat hepatocarcinogenesis (Allen, 1982), the inhibitory effect of disulfiram on various carcinogens may be related to its inhibitory effect on aldehyde dehydrogenases.

Disulfiram was shown to protect mice against ifosfamide- and cyclophosphamide-induced urotoxicity when administered simultaneously with said drugs without compromising their anti-tumor activity against Sarcoma 180, EL-4 leukemia or L1210 murine leukemia (Hacker, 1982; Ishikawa, 1991; Ishikawa, 1994). On the other hand, disulfiram did not show any protection against cisplatin nephrotoxicity in humans (Verma, 1990). Disulfiram protected rats against the toxic side effects of 1-(2-hydroxyethyl)-3-(2-chloroethyl)-3-nitrosourea (HECNU), without inhibiting its anti-tumor potency (Habs, 1981). Disulfiram was also shown to potentiate the anti-cancer activity of some agents such as to nitrogen mustard (HN2) cytotoxicity against murine leukemia at 3 mg/mouse (Valeriote, 1989).

Disulfiram, together with ascorbic acid, augmented inhibition of Meth A tumor cell proliferation in vitro by increasing the intracellular oxygen free radicals (Mashiba, 1990). In addition, disulfiram inhibited superoxide dismutase in vivo (Forman, 1980; Ohman, 1986). All of these could result in an increase in oxygen species toxic to the cell thereby making the cell more sensitive to damage by a variety of chemotherapeutic agents or radiation that produce superoxide anions species (Goodman, 1977). Resistance to cyclophosphamide and oxazaphosphorines is related to aldehyde dehydrogenase activity (Magni, 1996; Rekha, 1994), and inhibition of this enzyme by disulfiram thus increase sensitivity to these chemotherapies.

U.S. Pat. No. 4,870,101 (Ku and Doherty, 1989) discloses a method for inhibiting the release of interleukin-1 in animals which comprises administering to said animals an amount of disulfiram effective to inhibit the release of interleukin-1, thus proposing disulfiram for the treatment of IL-1 mediated inflammations such as psoriasis, rheumatoid arthritis, diabetes and atherosclerosis.

Disulfiram, given 0.05% in diet for 2 years, did not increase any tumor type in rats (Cheever, 1990). The toxic dose for disulfiram in normal mice is about 6–10 mg/mouse/day. The $LD_{50}$ of disulfiram given orally in rats is 8.6 g/Kg.

None of the above publications describes or suggests the use of disulfiram as an inhibitor of angiogenesis.

SUMMARY OF THE INVENTION

It has now been found in accordance with the present invention that disulfiram inhibits angiogenesis and is able to block neovascularization induced subcutaneously in nude mice.

The present invention thus relates to the use of disulfiram for the preparation of a pharmaceutical composition useful for inhibition of angiogenesis.

The pharmaceutical composition of the invention is suitable for treatment of angiogenesis-dependent diseases including, but not being limited to, ophthalmologic disorders such as diabetic retinopathy, corneal graft neovascularization, neovascular glaucoma, trachoma and retinopathy of prematurity also known as retrolental fibroplasia, dermatologic disorders such as dermatitis and pyogenic granuloma, pediatric disorders such as hemangioma, angiofibroma, and hemophilic joints, orthopedic disorders such as nonunion fractures, neurologic cerebrovascular disorders such as arteriovenous malformation, neoplasms such as leukemia and solid tumors, connective tissue disorders such as scleroderma, and treatment of hypertrophic scars.

Examples of solid tumors that can be treated with disulfiram according to the invention include, but are not limited to, bladder, breast, cervix, ear, esophagus, kidney, larynx, liver, lung, ovary, pancreas, prostate, skin, stomach, thyroid, urethra and uterus carcinomas.

For the preparation of the pharmaceutical compositions of the invention, disulfiram is mixed with pharmaceutically acceptable carriers and conventional excipients to produce unit dosage formulations suitable for administration. Any suitable mode of administration is envisaged by the invention, but oral administration is preferred.

The dosage of disulfiram to be administered daily will depend on the disorder being treated and the age, weight and condition of the patient being treated, and can be determined without difficulty by skilled physicians. Based on the examples herein performed in animals, it can be deduced that dosages between 1–50 mg/person are suitable for humans.

In another aspect, the invention relates to a method for inhibiting angiogenesis in a mammal, particularly humans, which comprises administering to a mammal in need thereof an amount of disulfiram effective for inhibiting angiogenesis.

In still another aspect, the invention relates to the use of disulfiram to prevent cell hyperproliferation and formation of clots along or around medical devices such as stents, catheters, cannulas, electrodes, and the like. In one embodiment, disulfiram may be systemically administered to a patient in which such a device has been inserted. In another embodiment, the medical device is coated with disulfiram before insertion in the patient, and such disulfiram-coated medical devices are also envisaged by the present invention.

Abbreviations: BCE: bovine capillary endothelial cells; bFGF: basic fibroblast growth factor; BSMC: bovine vascular smooth muscle cells; DMEM: Dulbecco's Modified Eagle's Medium; EGF: epidermal growth factor; FCS: fetal calf serum; GPS: glutamine/penicillin/streptomycin; HB-EGF: heparin-binding epidermal growth factor.

BRIEF DESCRIPTION OF THE DRAWINGS

FIGS. 1A–1C show inhibition of neovascularization in nude mice by disulfiram (D). Agarose beads containing the angiogenic compound bFGF (10 $\mu$g/bead) were implanted subcutaneously in nude mice and the angiogenic potential of bFGF in vivo was demonstrated 4 days after implantation, in skin specimens (FIG. 1B). Saline, as a negative control, did not induce neovascularization around the bead (FIG. 1A). Disulfiram (D) introduced systemically at 60 $\mu$g/mouse inhibited almost completely neovascularization induced by bFGF inside and around the bead (FIG. 1C). Bar is one mm.

DETAILED DESCRIPTION OF THE INVENTION

Vascular smooth muscle cells and endothelial cells are the two cell types constituting the blood vessel walls. Angiogenesis, the growth of new capillary blood vessels by sprouting from established vessels, requires the growth of vascular endothelial cells and vascular smooth muscle cells. According to the data of the present invention, disulfiram is clearly identified as an effective inhibitor of angiogenesis.

Thus, as shown herein, disulfiram inhibited in vivo the induction of new blood vessels in the mouse skin and was effective when administered orally. The ability of disulfiram to inhibit at low concentrations the growth of cultured capillary endothelial cells (BCE) suggests that the drug acts directly on capillary endothelial cells. Moreover, the inhibition of endothelial cell growth was shown to be non-reversible. The growth of vascular smooth muscle cells (BSMC), another cell constituent of the blood vessel wall, was also inhibited by disulfiram at low concentrations (0.5 $\mu$M). The fact that the drug induces apoptosis in capillary endothelial cells and fails to induce apoptosis in other cell types such as vascular smooth muscle cells, keratinocytes (MK), fibroblasts and C6 rat glioma cells, indicates that it has some specificity for capillary endothelial cells. Indeed, when disulfiram was administered systemically at low doses of 25–60 $\mu$g/mouse, the formation of new blood vessels was specifically disrupted, while no evidence for damage in other tissues was observed. The low concentration of disulfiram administered systemically when calculated for the volume of a mouse (3 $\mu$M), was in the range of that used in vitro for endothelial cells (0.1–0.2 μM), especially when the metabolic processing of the drug in the body is taken into account.

As might be expected from its ability to inhibit capillary endothelial cells and BSMC at concentrations achievable in vivo, systemic treatment of mice with disulfiram inhibited neovascularization in the skin. The growth of C6 rat glioma cells in vitro was inhibited by disulfiram. Taken together with the fact that active angiogenesis is essential for the progressive growth of solid tumors (Folkman, 1990) and that C6 glioma tumor development is angiogenesis-dependent (Abramovitch, 1995; Ikeda, 1995; Niida, 1995; Plate, 1992), one could expect that C6 glioma tumor growth would be affected by disulfiram. Indeed, disulfiram significantly reduced both Lewis lung metastasis in the lungs and C6 tumor development in vivo when administered systemically per os at low concentrations similar to those observed to be effective in vitro, both for endothelial and C6 glioma cells, suggesting that the inhibitory activity for C6 tumor growth and for metastasis in the lungs in vivo is induced through inhibition of angiogenesis and of C6 glioma cell growth. Once ingested and absorbed through the intestinal tract or injected intraperitoneally, disulfiram is extensively distributed throughout the body including the brain (Faiman, 1978), but the mechanism through which disulfiram induces its inhibitory effects in vitro or in vivo is not known. Also the reason for capillary endothelial cells being more liable to disulfiram than other cell types for induction of apoptosis, is not known.

The results shown here demonstrate that disulfiram inhibits capillary endothelial and vascular smooth muscle cell growth and induces apoptosis in capillary endothelial cells and that, when used systemically in mice, disulfiram inhibits angiogenesis and decreases C6 glioma tumor growth, clearly defining disulfiram as a new inhibitor of angiogenesis and showing its potential use for therapy in angiogenesis-dependent diseases such as pathologies in which neovascularization is involved, including neoplasia.

The invention will now be illustrated by the following non-limiting examples.

EXAMPLES

Materials and Methods (a) Materials:

Disulfiram (Sigma) and mouse EGF (Collaborative Biomedical Products, Bedford, Mass., U.S.A.) were purchased. Recombinant b-FGF and recombinant HB-EGF were kindly provided by Prof. Gera Neufeld, and by Dr. Judith A. Abraham (Scios Nova Inc., Mountain View, Calif.), respectively.

(b) Cell lines:

C6 rat glioma cells were routinely cultured in DMEM supplemented with 5% FCS (Biological Industries, Israel), GPS (100 U/ml penicillin, 100 mg/ml streptomycin (Biological Industries, Israel) and 2 mM glutamine (Biolab Ltd. Israel)) and 125 μg/ml fungizone (Biolab Ltd, Israel).

Brain bovine capillary endothelial cells (BCE) and bovine vascular smooth muscle cells (BSMC), kindly provided by Prof. Israel Vlodavsky (Hadassah Medical School, Jerusalem, Israel), were cultured at 37° C. in low glucose DMEM (1 g/liter) supplemented with 10% calf serum (HyClone, Logan, Utah, U.S.A.), a serum-free supplement: biogro-1 (Beth Haemek, Israel) and GPS.

Bovine aortic vascular smooth muscle cells (BSMC) were cultured in low glucose DMEM (1 g/liter) supplemented with 10% FCS (HyClone, Logan, Utah) and GPS.

The BALB/MK epidermal keratinocyte cell line, kindly provided by Dr. S Aaronson (National Cancer Institute, Bethesda, Md., USA), was cultured (37° C., 10% $CO_2$ humidified atmosphere) in calcium-free MEM (Beth Haemek, Israel) supplemented with 10% dialyzed FCS and murine EGF (5 ng/ml).

(c) Measurement of DNA synthesis

C6 rat glioma cells were plated in 96-well plates (Nunc, Denmark) (5000 cells per well) in DMEM with 5% FCS. After 6 hours the cells were rinsed and incubated for 48 hours in serum free medium. 5% FCS or growth factors were then added to the cells for 24 hours (triplicates). $^3$H-methyl-thymidine (5μCi/ml) (Rotem Ind. Ltd., Israel) was added to the cells for the last 14 hours. The cells were rinsed with 100 μl methanol for 10 minutes, followed by 200 μl 5% trichloroacetic acid, and then rinsed and lysed with 150 μl 0.3M NaOH. Radioactive thymidine incorporated into the DNA was determined for 1 min with 3 ml scintillation liquid (ULTIMA GOLD Packard) in a β-counter. DNA synthesis assays were performed in triplicates.

Bovine capillary endothelial cells (BCE) and bovine aortic BSMC were plated in 24-well plates (6000 cells per well) in 500 μl DMEM medium supplemented with 10% Colorado calf serum (CCS) (GIBCO, USA) and GPS. After 24 hours, medium was changed to starvation medium (2% CCS, 0.5% BSA, GPS) for 24 hours. $^3$H-methyl-thymidine (5 μCi/ml) was added for the last 6 hours. DNA synthesis assays were performed as described above, in triplicates. DNA synthesis assays in BALB/MK keratinocytes were performed as previously described (Marikovsky, 1995).- DNA synthesis assays were performed in triplicates.

Disulfiram was prepared in 0.1 mM stock solutions in DMSO. Control samples were incubated with the appropriate concentration of DMSO. Inhibition was calculated as percentage of DNA synthesis of control.

(d) Subcutaneous angiogenesis in nude mice

Spherical agarose beads of approximately 1 mm in diameter were formed from 4% low gelling temperature agarose (Sigma) in PBS containing b-FGF or HB-EGF as angiogenic agent. The candidate angiogenic agent (10 μg/bead) was warmed in sterile microtest tubes to 40° C. in a dry-bath for a few seconds. 10 μl of agarose solution (6% in saline, 45° C.) were then added to 5 μl of the angiogenic compound and beads were formed above ice using a 20 μl pipette tip. Beads were implanted subcutaneously 1 cm away from the incision-site as reported previously for multicellular spheroids (Abramovitch, 1995) in mice anesthetized with a single dose of 75 mg/kg ketamine+3 mg/kg xylazine (i.p.). Experiments were carried out for 4 days in CD1 nude male mice. Each day one ml of aqueous solutions with or without 0.1–0.25 mM (25–60 μg) disulfiram was introduced per os to the mice using a feeding needle. Treatment was for three days starting from the day of bead implantation until one day before termination. Experiments were done in quadruplicates and repeated three times.

(e) Growth of C6 glioma tumors

C6 rat glioma cells ($10^6$) were injected subcutaneously into the back of the neck of CD1 nude male mice. After 3 days, 1 ml of aqueous solutions with or without 0.1–0.5 mM disulfiram (25–120 μg) was introduced per os to the mice using a feeding needle. Mice were orally fed three times per week. Tumors were removed 30 days following C6 cells injection, weighed, fixed in buffered formalin and histological sections were prepared. Each experimental group included 8 animals, and experiments were repeated twice.

(f) Growth of Lewis lung carcinoma tumors

The Lewis lung carcinoma (3LL), which originated spontaneously in a C57/BL/6J ($H-2^b$) mouse, is a malignant tumor that produces spontaneous lung metastases. The metastatic clone D122, kindly provided by Prof. Lea Eisenbach (Weizmann Institute of Science, Rehovot, Israel), was used herein for tissue culture and for in vivo experiments. The cell cultures were maintained in DMEM supplemented with 10% heat-inactivated FCS, glutamine, antibiotics, sodium pyruvate and nonessential amino acids.

Two metastasis models were used: 1. The footpad model. 2. The i.v. model. The assay of tumor development in the footpad model and evaluation of lung metastases was done as previously described (Eisenbach, 1983). Briefly, eight mice in each experimental group were inoculated with $2 \times 10^5$ D122 cells in 0.05 ml PBS in the right hind footpad. Three days following tumor cells injection, mice were treated per os by disulfiram or saline 3 times per week. The tumors became palpable within 11–19 days. Local tumor growth was determined by measuring the footpad diameter with a calipers. At 26–40 days following inoculation, when local tumor reached a diameter of 6–7 mm, mice were anesthetized with a single dose of 75 mg/kg ketamine+3 mg/kg xylazine (i.p.) and the tumor-bearing leg was removed by amputation above the knee joint. To measure progress of metastases the mice were killed 24 days following amputation by injecting 20 mg/mouse xylazine i.p. and lungs were weighed.

To distinguish between the effect on the migration of the cells from the main tumor and the development of a tumor from a metastatic foci, the i.v. model was used. D122 cells ($5 \times 10^5$) were injected i.v. to the tail of C57/B1 male mice and after 24 days mice were killed and their lungs weighed. Treatment with disulfiram was started 3 days following the injection of D122 cells. Each experimental group included 8 animals, and experiments were repeated twice.

(g) Analysis of apoptotic cells by FACS

Cells were cultured in plastic tissue culture dishes for 48 hours in presence of growth media as described above, until reaching 40–50% confluency. Disulfiram was then added to the cells for 20 hours. The cells were removed from the plates by EDTA-trypsin and fixed in ice-cold 70% ethanol (BioLab, Israel) in $-20°$ C. for 2 hr to overnight. The fixed cells ($2-5 \times 10^6$) were washed once with HEPES-buffered saline (HBSS) and incubated with 0.5 mg/ml RNAseH (Boehringer Mannheim). Afterwards the cells were resuspended in HBSS containing 50 µg/ml propidium iodide (Sigma) and subsequently analyzed on a FACSort flow cytometer (Beckton Dickinson Inc.) using Lysis II software. For the analysis, 10,000 cells were examined from each sample. The percentage of the hypodiploid cells was measured (Darzynkiewicz, 1992; Afanasyev, 1993). The cell cycle histogram was divided into four regions according to the cell cycle phases: Ap, apoptotic cells; $G_1$, diploid cells; S, intermediate cells; and $G_2/M$, tetraploid cells.

(h) TUNEL assay for apoptosis

Cells were cultured on microscope slides for 48 hours in presence of growth media as described above, until reaching 40–50% confluency. Disulfiram was then added to the cells for 6 hours or for 20 hours in the case of BALB/MK keratinocytes, fixed with 4% paraformaldehyde and washed three times with PBS. Apoptosis was analyzed by the in situ TUNEL staining carried out as described (Wride, 1994). Briefly, microscope slides were incubated for 15 min in 2×SSC buffer at 60° C., washed in DDW and incubated with 20 µg/ml proteinase K (Boehringer Mannheim) for 15 min at room temperature. After a wash with DDW, endogenous peroxidases were inactivated by incubating the slides with 2% $H_2O_2$ in PBST (PBS with 0.05% Tween 20) for 10 min at room temperature. Slides were then incubated in TdT buffer (Boehringer Mannheim) for 5 min at room temperature, and a reaction mixture containing 5×TdT buffer and 1 µl biotin-21-dUTP (Clontech, 1 mM stock) and 8 units of the TdT enzyme (Boehringer Mannheim) in total volume of 50 µl was subsequently added. The reactions were carried out at 37° C. for 1.5 hr in a humid chamber. The slides were washed in 2×SSC, DDW and finally with PBS and covered with 10% skim milk in PBST for 15 min. After removal of the skim milk, the sections were incubated with ABC solution from ABC kit (Vector Laboratories, Inc.) for 30 min at room temperature, washed with PBS and stained using AEC procedure (Sigma) The slides were then washed ×3 in DDW and stained with haematoxylin for 30 sec and mounted by Kaiser's glycerol gelatin (Merck).

Example 1

In Vivo Inhibition of Neovascularization by Disulfiram

Figure 1:
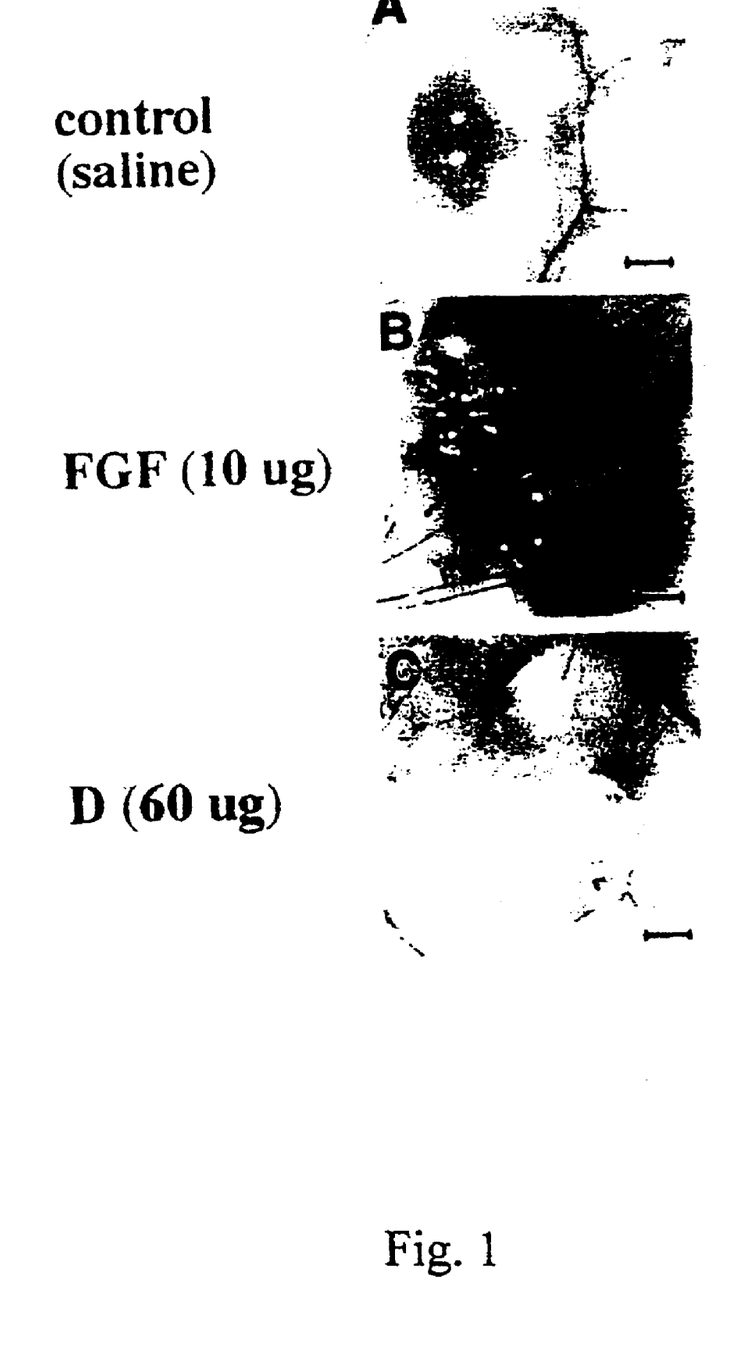

Agarose beads containing the angiogenic factor bFGF (10 µg/bead) were implanted subcutaneously into CD1 nude mice as described in section (d) of "Materials and Methods" above. The results are shown in FIG. 1. After 4 days new blood vessels clearly developed around and inside the beads containing bFGF (FIG. 1B) while the control beads containing only saline appeared clear and without any new blood vessels being formed around or within the beads (FIG. 1A). However, when the mice were daily fed per os during 3 days with 1 ml aqueous solution (0.1–0.25 mM) of disulfiram (D) (25–60 µg/mouse/day), angiogenesis around the beads containing bFGF was clearly inhibited (FIG. 1C).

Example 2

Disulfiram Inhibits Capillary Endothelial Cell Proliferation

Figure 2:
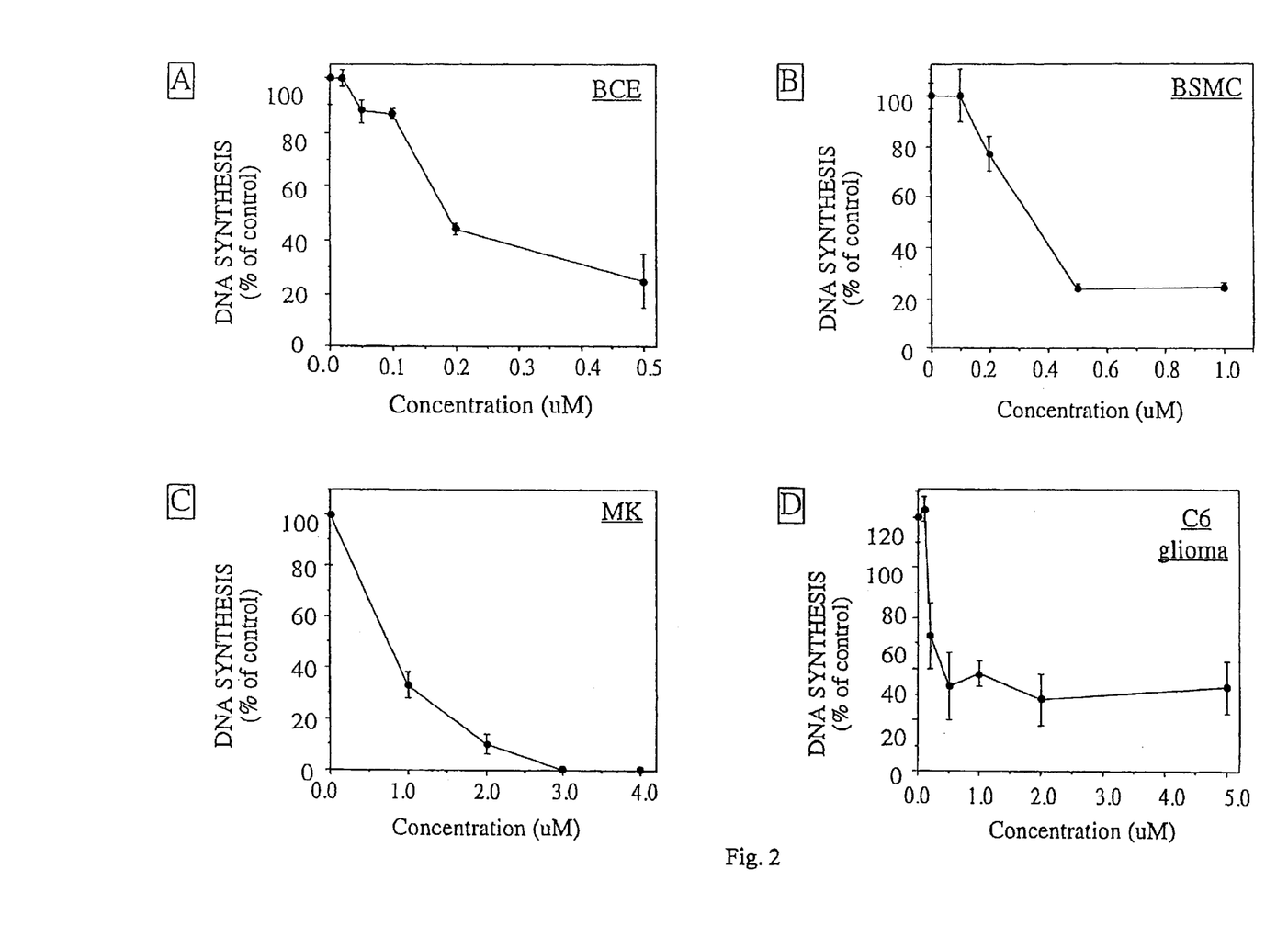
FIGS. 2A–2D show in vitro inhibition of DNA synthesis by disulfiram in a dose-dependent manner in BCE, BSMC, BALB/MK and C6 rat glioma cells, respectively, as measured by incorporation of $^3$H-thymidine into the cells. Experiments were done in triplicates and the inhibition was calculated as percentage of DNA synthesis of non-treated control.

To determine whether disulfiram acts directly on endothelial cells rather than on accessory cells such as macrophages and mast cells that can be responsible for the development of an angiogenic response in vivo, the effect of the drug on the growth of BCE cells was examined in vitro as described in section (c) of "Materials and Methods" above. DNA synthesis in BCE cells was measured in presence of increasing concentrations of disulfiram incubated for 24 hours with the cells. The results are shown in FIG. 2 At. concentrations ranging from 0.1–0.5 µM, disulfiram was able to inhibit DNA synthesis in BCE cells in a dose dependent manner, complete inhibition being achieved at 0.5 µM disulfiram (FIG. 2A). BCE cells were shown to be more sensitive to the inhibitory activity of disulfiram than other cell types such as BALB/MK keratinocytes (FIG. 2C), C6 rat glioma cells (FIG. 2D) or bovine aortic vascular smooth muscle cells (BSMC) (FIG. 2B). Maximal inhibitory activity (80%) for BSMC was at 0.5–1 µM disulfiram, while maximal inhibitory activity for C6 glioma cells or BALB/MK keratinocytes was at concentrations 10 fold higher (2–3 µM) than those for endothelial cells (0.2–0.5 µM). At higher concentrations (>10 µM), disulfiram became less inhibitory for all cell types examined (not shown).

Figure 3:
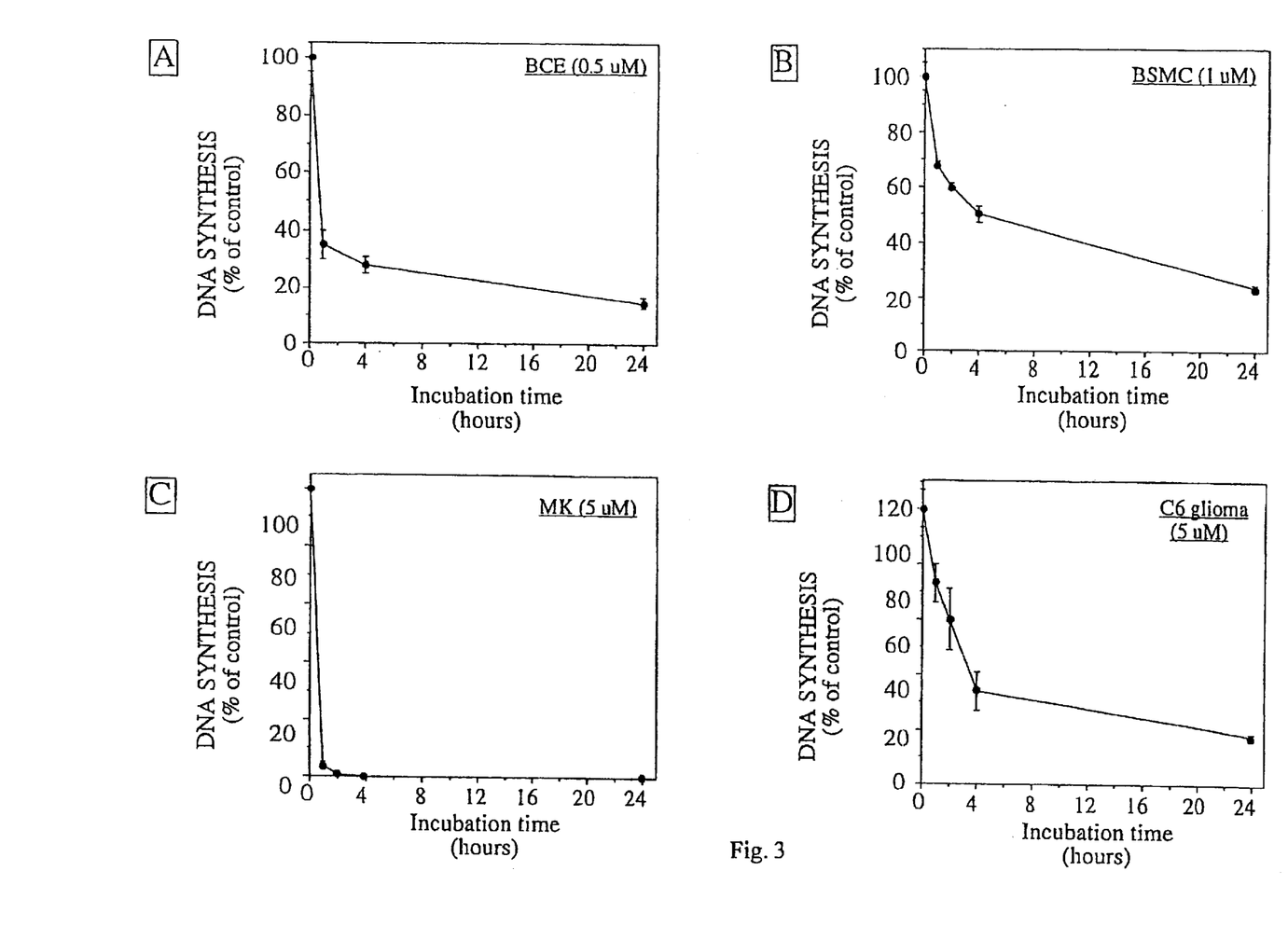
FIGS. 3A–3D show inhibition of DNA synthesis in a non-reversal manner by disulfiram at various periods of time (1, 2, 4 and 24 hours) in BCE, BSMC, BALB/MK and C6 rat glioma cells, respectively, as measured by the incorporation of $^3$H-thymidine into the cells. Experiments were done in triplicates and the inhibition was calculated as percentage of DNA synthesis of non-treated control.

To examine the time course of the effect of disulfiram and whether the effect was reversible, cells were incubated with disulfiram for various periods of time (1, 2, 4 and 24 hours), then washed away and DNA synthesis was determined. One to 4 hours of exposure to disulfiram were enough to induce maximal inhibitory effect at concentrations ranging from 0.5 µM for BCE cells (FIG. 3A) to 5 µM for BALB/MK keratinocytes (FIG. 3C) and C6 glioma cells (FIG. 3D). As shown, for BCE, MK and C6 glioma cells the inhibitory effect seemed to be maintained even 24 hours following short exposure to the drug. BCE cells were most sensitive: 1–2 hours of incubation with as low as 0.5 $\mu$M disulfiram were enough to induce near maximal inhibition of DNA synthesis (FIG. 3A). BSMC were less sensitive as far as time course is concerned when incubated with 1 $\mu$M disulfiram. Following 4 hours of incubation with 1 $\mu$M disulfiram, DNA synthesis inhibition in BSMC reached only 50% (FIG. 3B). The data shown here indicate that the damage for capillary endothelial cells, following a short incubation of 1 to 2 hours, was maximal and that, at least in a time scale of 24 hours, this damage was non-reversible.

Example 3

Inhibition of Endothelial Cell Proliferation by Disulfiram is Via Apoptosis

To determine whether the non-reversible inhibition of capillary endothelial cells was induced by the programmed cell death pathway, apoptosis in BCE cells was examined by means of the FACS analysis and by the TUNEL method.

Figure 4:
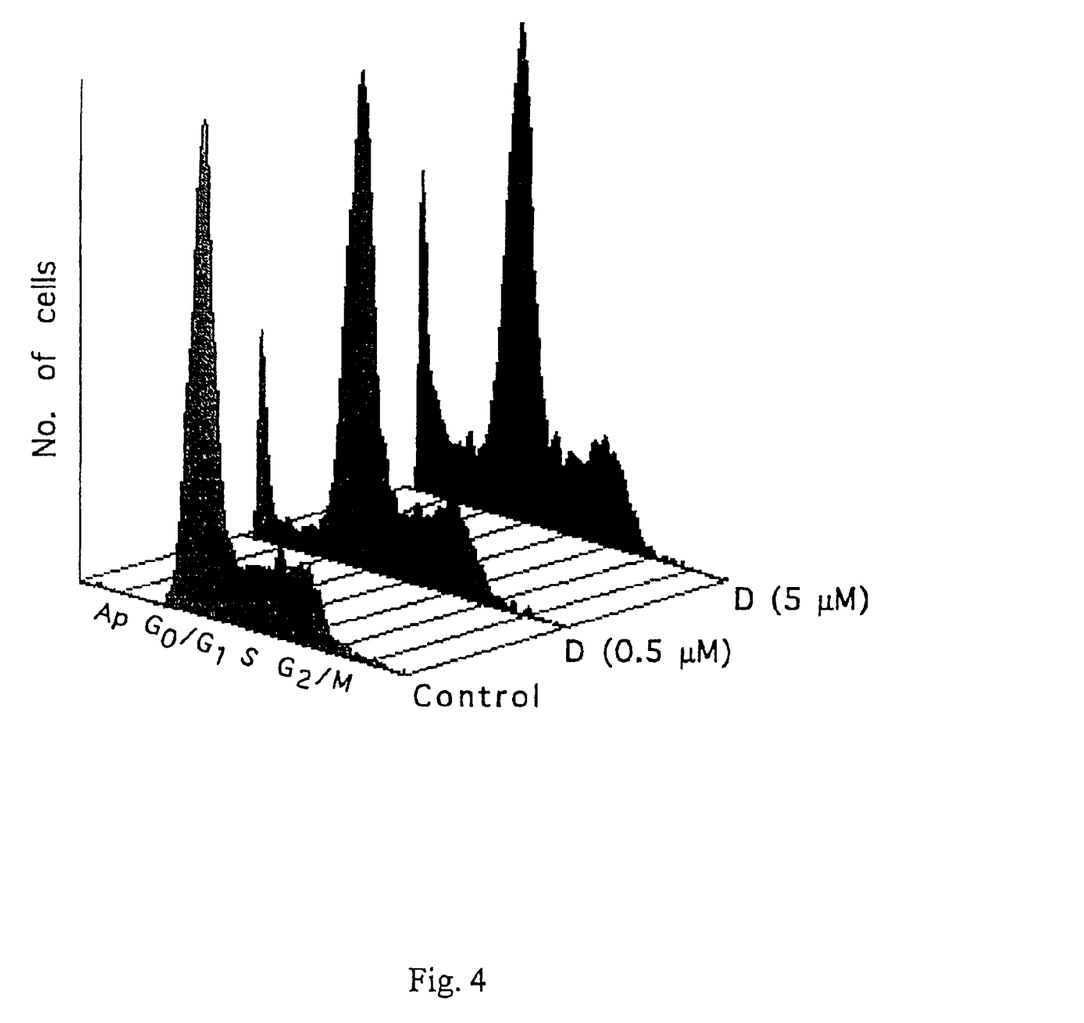
FIG. 4 shows disulfiram-induced apoptosis in endothelial cells. BCE cells were incubated with 0.5–5 $\mu$M disulfiram (D) for 20 hours and analyzed by FACS for the DNA content of the cells. Disulfiram induced in a dose-dependent manner a sub-diploid apoptotic population of endothelial cells, that was not apparent in control-treated cells. Experiments were repeated twice with triplicates.

Capillary endothelial cells were grown during 48 hours to 40–50% confluency and disulfiram was then added to the cells for 20 hours as described in section (g) of "Materials and Methods" above. The results are shown in FIG. 4. FACS analysis of the DNA content of endothelial cells incubated with 0.5–5 $\mu$M disulfiram demonstrated the appearance of a sub-diploid apoptotic population of cells. The abundance of apoptotic cells was dose-dependent. In contrast, control non-treated endothelial cells did not undergo this DNA degradation process and most of the cells were in the $G_0/G_1$ phase and some in the S and $G_2/M$ phase. Unlike capillary endothelial cells, BALB/MK keratinocytes treated with 4 $\mu$M disulfiram and analyzed by FACS, did not exhibit induction of apoptosis (not shown). Typically for cells undergoing apoptosis, endothelial cells treated with disulfiram quickly became rounded. In contrast, 3T3 fibroblasts, C6 glioma cells or BSMC treated with 1 $\mu$M, 2 $\mu$M or 5 $\mu$M, respectively, of disulfiram, did not change their shape to the rounded form.

Figure 5:
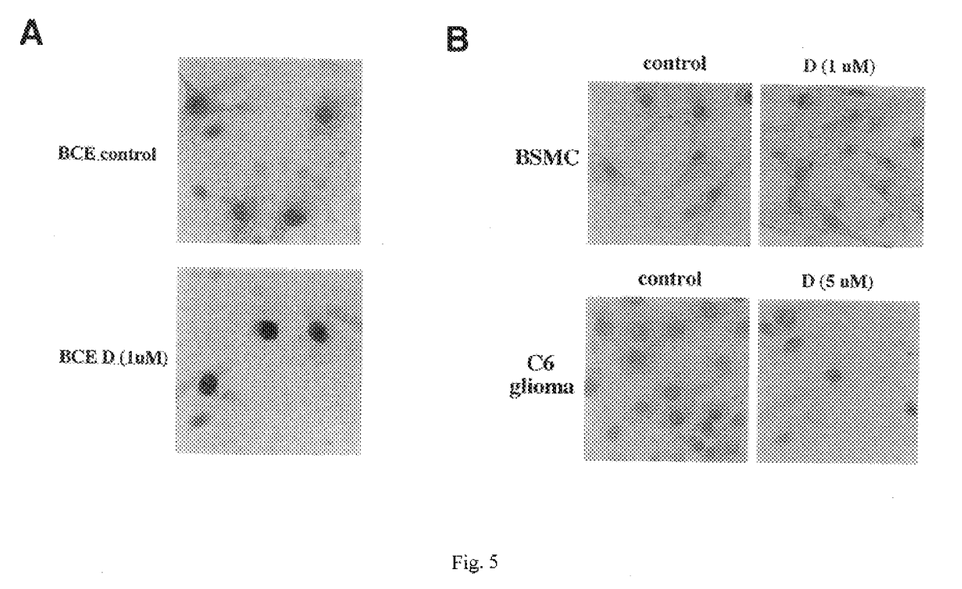
FIGS. 5A–5B show disulfiram-induced apoptosis in BCE, BSMC and C6 glioma cells, following incubation with the indicated concentrations of disulfiram (D) for 6 hours, as analyzed by the TUNEL method. The nuclei of BCE cells (FIG. 5A, bottom) treated with disulfiram were labeled using the TUNEL staining method, while the nuclei of control BCE (FIG. 5A, top) and of BSMC (FIG. 5B, top) and C6 glioma cells (FIG. 5B, bottom) treated with disulfiram were not labeled using the TUNEL staining method. Experiments were repeated twice with triplicates.

The TUNEL method was used to label the nuclei of cells undergoing apoptosis as described in section (h) of "Materials and Methods" above. The results are shown in FIG. 5. As shown in FIG. 5A, bpttom, capillary endothelial (BCE) cells incubated for 6 hours with 1 $\mu$M disulfiram were induced into apoptosis. In contrast, disulfiram did not induce BSMC (1 $\mu$M) (FIG. 5B, top), BALB/MK keratinocytes (5 $\mu$M) (not shown) and C6 rat glioma cells (5 $\mu$M) (FIG. 5B, bottom) into apoptosis following incubation for 6 hours, as measured by the TUNEL method. Capillary endothelial cells are, thus, distinct in their apparent sensitivity to disulfiram-induced apoptosis.

Example 4

Disulfiram Inhibits Lewis Lung Carcinoma and C6 Glioma Tumor Growth in Vivo

Since disulfiram was shown to be an effective inhibitor of neovascularization in vivo as well as inhibitory to C6 glioma cell growth in vitro, one could expect that systemic treatment with the drug may slow tumor development, since active angiogenesis is essential for the progressive growth of solid tumors beyond a diameter of a few millimeters (Folkman, 1990).

Figure 6:
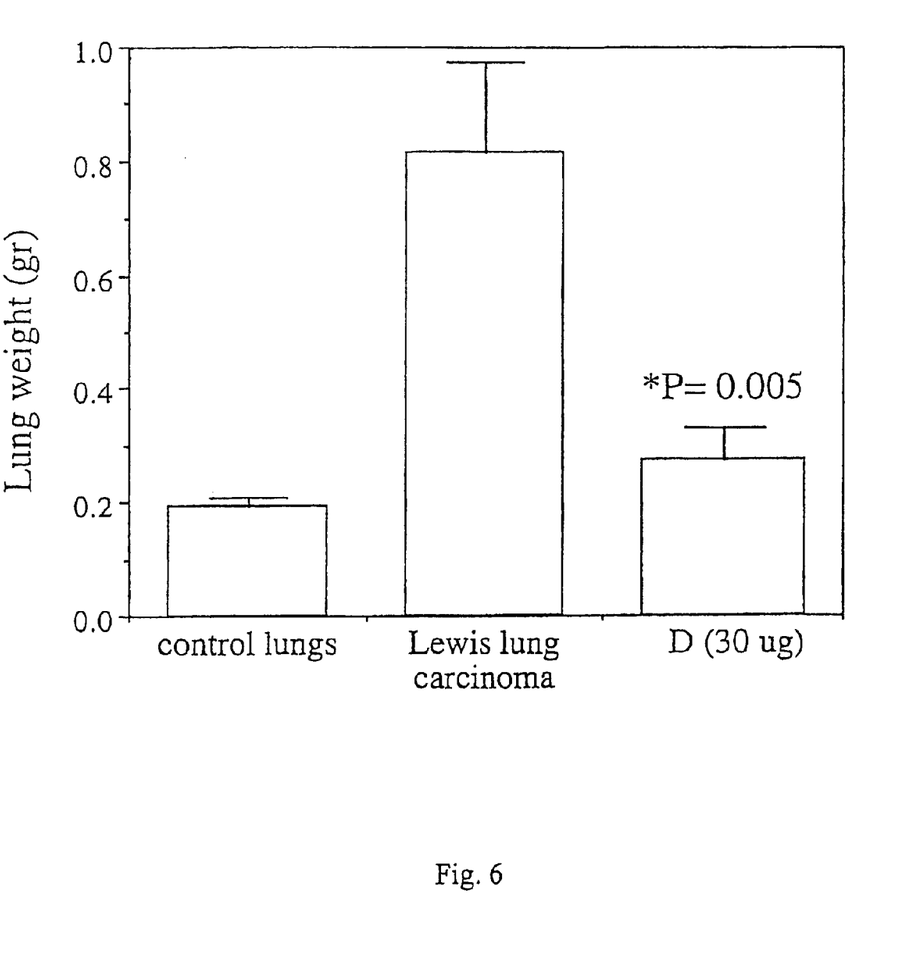
FIG. 6 shows inhibition by disulfiram of Lewis lung tumor metastasis in the lungs of mice in the footpad model. Lungs from C57/BL mice fed systemically 3 times a week with disulfiram (30 $\mu$g) were weighed 24 days following removal of the tumor-bearing leg. The weight of the lungs from normal mice was subtracted from that of the metastasized lungs. Compared with water-fed control, metastasis on the lungs of disulfiram-treated animals was significantly smaller (n=6) p=0.005.

The effect of disulfiram was thus examined in the Lewis lung carcinoma footpad model in C57/BL mice as described in section (f) of "Material and Methods" above, using concentrations that were shown to be inhibitory for angiogenesis in vivo. Twenty-four days following the removal of the tumor-bearing leg, lungs were weighed. Metastasis in the lungs was significantly retarded by systemic treatment with disulfiram. In the control non-treated group, 50% of the mice died before or on the 24th day following the removal of the tumor-bearing leg, while no disulfiram-treated mice died. Moreover, two out of six mice in the disulfiram-treated group had no metastases at all. As shown in FIG. 6, treatment with disulfiram at concentrations of 30 $\mu$g/mouse lowered the metastatic load in the lungs by almost 10-fold. At higher concentrations (120 $\mu$g/mouse) there was only slight decrease in the metastatic load in the lungs (not shown).

Similarly, the effect of disulfiram was examined in a C6 rat glioma model in CD1-nude mice as described in section (e) of Materials and Methods above, using concentrations that were shown to be inhibitory for angiogenesis in vivo. Tumors from mice fed systemically 3 times a week with disulfiram were weighed 30 days following administration of C6 rat glioma cells to CD1 nude mice. The growth of the tumors was significantly retarded by systemic treatment with disulfiram. Compared with water-fed control, tumors from animals treated with disulfiram were significantly smaller. Experiments were repeated twice (n=8).

As shown in Table 1, at disulfiram (DSF) concentrations of 25–120 $\mu$g/mouse, tumor development was retarded by 57–38%, respectively. Interestingly, the most effective concentration was the lowest one. This is in agreement with the data observed that disulfiram became less inhibitory for in vitro cell growth at high concentration (not shown). Since disulfiram inhibits angiogenesis both in vivo in mice and in vitro in C6 glioma cells, it can be assumed that tumor growth inhibition observed for disulfiram is the result of its dual action, one on the neovascularization of the tumor and one on the C6 glioma cells. Pathological examination of various tissues (kidney, liver, stomach, lungs and spleen), including histological sections prepared from these tissues, revealed no effect on these tissues in the treated animals. Blood vessels examined in these tissues were also not affected.

TABLE 1

Disulfiram inhibits C6 rat glioma tumor growth in nude mice

|  | (n) | Tumor weight (g)[a] | % inhibition | p value[b] |
|---|---|---|---|---|
| Control | (8) | 1.37 ± 0.21 | 0 |  |
| DSF (25 $\mu$g) | (8) | 0.59 ± 0.08 | 57 | p = 0.003 |
| DSF (120 $\mu$g) | (8) | 0.84 ± 0.18 | 38 | p < 0.05 |

[a]Tumors were weighed 30 days following administration of C6 rat glioma cells into nude mice.
Indicated values are mean of (n) animals ± SEM.
[b]Significance of difference between control and treated animals as determined by Student's test.

Example 5

Disulfiram Inhibits Lewis Lung Metastasis in the I.V. Model

To distinguish between the effect on the migration of the cells from the main tumor and the development of a tumor from a metastatic foci, the i.v. metastastis model was used as described in section (f) of materials and Methods above. D122 cells were injected i.v. to the tail of C57/B1 male mice. Three days after, disulfiram was administered to the mice per os 3 times per week, at concentrations of 13–40 $\mu$g/mouse.

Figure 7:
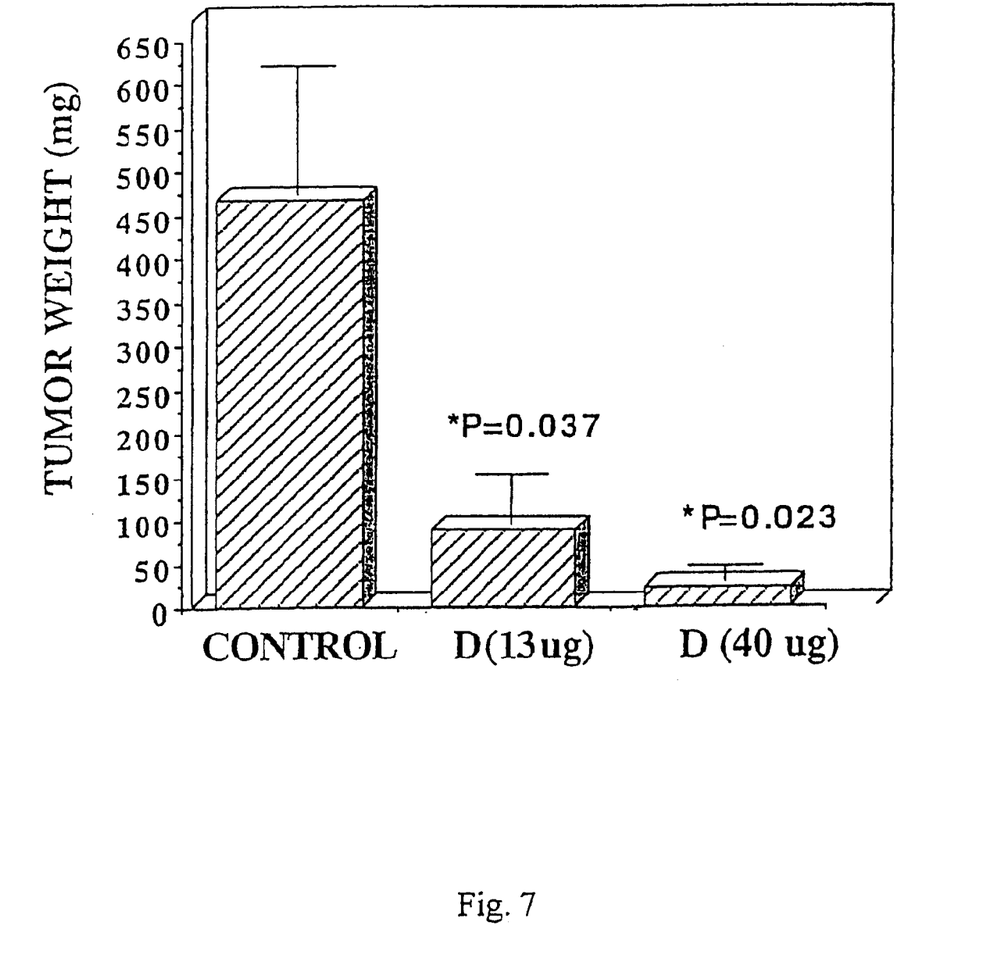
FIG. 7 shows inhibition by disulfiram of Lewis lung tumor metastasis in the lungs of mice in the i.v. model. Lungs from C57/BL mice fed systemically 3 times a week with disulfiram (13–40 $\mu$g) were weighed 24 days following injection of D122 tumor cells i.v. The weight of the lungs from normal mice was subtracted from that of the metastasized lungs. Compared with water-fed control, metastasis in the lungs of disulfiram-treated animals was significantly smaller (n=6) (p=0.023–0.037). At 13–40 $\mu$g/mouse disulfiram decreased metastasis to the lungs 6–19 fold accordingly. Experiments were repeated twice.

As shown in FIG. 7, disulfiram inhibited 83–95% of the development of metastatic foci in the lungs. The fact that disulfiram was highly inhibitory to lung metastasis even in the i.v. model indicates that its inhibitory effect does not occur on the migratory phase of the cells but rather during foci development.

REFERENCES

1. Abramovitch, R. Meir, G., and Neeman, M. (1995). Neovascularization induced growth of implanted C6 glioma multicellular spheroids: magnetic resonance microimaging. Cancer Res 55, 1956–62.
2. Afanasyvev, V. N., Korol, B. A., Matylevich, N. P., Pechatnikov, V. A., and Umansky, S. R. (1993). The use of flow cytometry for the investigation of cell death. Cytometry 14, 603–9.
3. Allen, B., and Lindahl, R. (1982). Sequential 2-acetylaminofluorene-phenobarbital exposure induces a cytosolic aldehyde dehydrogenase during rat hepatocarcinogenesis. Carcinogenesis 3, 533–8.
4. Borchert, P., and Wattenberg, L. W. (1976). Inhibition of macromolecular binding of benzo(a)pyrene and inhibition of neoplasia by disulfiram in the mouse forestomach. J. Natl. Cancer Inst. 57, 173–9.
5. Brien, J. F., and Loomis, C. W. (1983). Disposition and pharmacokinetics of disulfiram and calcuim carbimide (calcium cyanamide). Drug Metab Rev 14, 113–26.
6. Cheever, K. L., Cholakis, J. M., el Hawari, A. M., Kovatch, R. M., and Weisburger, E. K. (1990). Ethylene dichloride: the influence of disulfiram or ethanol on oncogenicity, metabolism, and DNA covalent binding in rats. Fundam. Appl. Toxicol. 14, 243–61.
7. Cohen, J. D., and Robins, H. I. (1990). Cytotoxicity of diethyldithiocarbamate in human versus rodent cell lines. Invest. News Drugs 8, 137–42.
8. Darzynkiewicz, Z., Bruno, S., Del Bino, G., Gorczyca, W., Hotz, M. A., Lassota, P., and Traganos, F. (1992). Features of apoptotic cells measured by flow cytometry. Cytometry 13, 795–808.
9. Eisenbach, L., Segal, S., and Feldman, M. (1983). MHC imbalance and metastatic spread in Lewis lung carcinoma clones. Int-J-Cancer 32, 113–20.
10. Eneanya, D. I., Bianchine, J. R., Duran, D. O., and Andresen, B. D. (1981). The actions of metabolic fate of disulfiram. Annu Rev Pharmacol Toxicol 21, 575–96.
11. Faiman, M. D., Dodd, D. E., and Hanzlik, R. E. (1978). Distribution of S35 disulfiram and metabolites in mice, and metabolism of S35 disulfiram in the dog. Res. Commun. Chem. Pathol. Pharmacol 21, 543–67.
12. Fiala, E. S. (1977). Investigations into the metabolism and mode of action of the colon carcinogens 1,2-dimethylhydrazine and azoxymethane. Cancer 40, 2436–45.
13. Folkman, J. (1990). What is the evidence that tumors are angiogenesis dependent? J. Natl. Cancer Inst 82, 4–6.
14. Forman, H. J., York, J. L., and Fisher, A. B. (1980). Mechanism for the potentiation of oxygen toxicity by disulfiram. J. Pharmacol. Exp. Ther. 212, 452–5.
15. Goodman, J., and Hochstein, P. (1977). Generation of free radicals and lipid peroxidation by redox cycling of adriamycin and daunomycin. Biochem. Biophys. Res. Commun. 77, 797–803.
16. Habs, H., and Habs, M. (1981). Effect of the pretreatment with disulfiram on the toxicity and antitumor activity of 1-(2-hydroxyethyl)-3-(2-chloroethyl)-3-nitrosourea in Sprague—Dawley rats. Cancer Lett. 13, 63–9.
17. Hacker, M. P., Ershler, W. B., Newman, R. A., and Gamelli, R. L. (1982). Effect of disulfiram (tetraethylthiuram disulfide) and diethyldithiocarbamate on the bladder toxicity and antitumor activity of cyclophosphamide in mice. Cancer Res. 42, 4490–4.
18. Haley, T. J. (1979). Disulfiram (tetraethylthioperoxydicarbonic diamide): a reappraisal of its toxicity and therapeutic application. Drug Metab Rev 9, 319–35.
19. Higashiyama, S., Abraham, J. A., Miller, J., Fiddes, J. C., and Klagsbrun, M. (1991). A heparin-binding growth factor secreted by macrophage-like cells that is related to EGF. Science 251, 936–9.
20. Ikeda, E., Achen, M. G., Breier, G., and Risau, W. (1995). Hypoxia-induced transcriptional activation and increased mRNA stability of vascular endothelial growth factor in C6 glioma cells. J. Biol. Chem 270, 19761–6.
21. Irving, C. C., Daniel, D. S., and Murphy, W. M. (1983). The effect of disulfiram on the carcinogenicity of N-butyl-N-(3-carboxypropyl)nitrosamine in the rat. Carcinogenesis 4, 617–20.
22. Irving, C. C., Tice, A. J., and Murphy, W. M. (1979). Inhibition of N-n-butyl-N-(4-hydroxybutyl)nitrosamine-induced urinary bladder cancer in rats by administration of disulfiram in the diet. Cancer Res. 39, 3040–3.
23. Ishikawa, M., Aoki, T., Yomogida, S., Takayanagi, Y., and Sasaki, K. (1994). Drug interaction effects on antitumour drugs (XV): Disulfiram as protective agent against cyclophosphamide-induced urotoxicity without compromising antitumour activity in mice. Pharmacol. Toxicol 74, 255–61.
24. Ishikawa, M., Takayanagi, Y., and Sasaki, K. (1991). Drug interaction effects on antitumour drugs (VIII): prevention of ifosfamide-induced urotoxicity by disulfiram and its effect on antitumour activity and acute toxicity of alkylating agents in mice. Pharmacol. Toxicol 68, 21–5.
25. Magni, M., Shammah, S., Schiro, R., Mellado, W., Dalla Favera, R., and Gianni, A. M. (1996). Induction of cyclophosphamide-resistance by aldehyde-dehydrogenase gene transfer. Blood 87, 1097–103.
26. Malejka Giganti, D., McIver, R. C., and Rydell, R. E. (1980). Inhibitory effect of disulfiram on rat mammary tumor induction by N-2-fluorenylacetamide and on its metabolic conversion to N-hydroxy-N-2-fluorenylacetamide. J. Natl. Cancer Inst 64, 1471–7.
27. Marikovsky, M., Vogt P., Eriksson, E., Rubin, J., Taylor, V., Sasse, J. and Klagsbrun, M. (1996). Wound-fluid derived heparin-binding epidermal growth factor (HB-EGF) is synergistic with IGF-1 for BALB/MK keratinocyte proliferation. J. Investig. Dermatology 106, 616–621.
28. Mashiba, H., and Matsunaga, K. (1990). Augmented inhibition of tumor cell proliferation in the combined use of disulfiram with ascorbic acid and the involvement of oxygen free radicals. Jpn. J. Exp. Med 60, 209–14.
29. Nigro, N. D., and Campbell, R. L. (1978). Inhibition of azoxymethane-induced intestinal cancer by disulfiram. Cancer Lett. 5, 91–5.
30. Nilda, H., Takeuchi, S., Tanaka, R., and Minakawa, T. (1995). Angiogenesis in microvascular endothelial cells induced by glioma cells and inhibited by tumor necrosis factor in vitro. Neurol. Med. Chir. Tokyo 35, 209–14.
31. Ohman, M., and Marklund, S. L. (1986). Plasma extracellular superoxide dismutase and erythrocyte Cu,Zn-containing superoxide dismutase in alcoholics treated with disulfiram. Clin. Sci 70, 365–9.
32. Plate, K. H., Breier, G., Weich, H. A., and Risau, W. (1992). Vascular endothelial growth factor is a potential tumour angiogenesis factor in human gliomas in vivo. Nature 359, 845–848.

33. Rao, A. R., Hussain, S. P., and Jannu, L. (1989). Modulation of 7,12-dimethyl-benz[a]anthracene-induced transmammary carcinogenesis by disulfiram and butylated hydroxyanisole in mice. Jpn-J-Cancer-Res 80, 1171–5.
34. Rekha, G. K., Sreerama, L., and Sladek, N. E. (1994). Intrinsic cellular resistance to oxazaphosphorines exhibited by a human colon carcinoma cell line expressing relatively large amounts of a class-3 aldehyde dehydrogenase. Biochem. Pharmacol 48, 1943–52.
35. Rotstein, J. B., and Slaga, T. J. (1988). Effect of exogenous glutathione on tumor progression in the murine skin multistage carcinogenesis model. Carcinogenesis 9, 1547–51.
36. Schmahl, D., Kruger, F. W., Habs, M., and Diehl, B. (1976). Influence of disulfiram on the organotropy of the carcinogenic effect of dimethylnitrosamine and diethylnitrosamine in rats. Z. Krebsforsch. Klin. Onkol. Cancer Res. Clin. Oncol. 85, 271–6.
37. Valeriote, F., and Grates, H. E. (1989). Potentiation of nitrogen mustard cytotoxicity by disulfiram, diethyldithiocarbamic acid, and diethylamine in mice. Cancer Res 49, 6658–61.
38. Verma, S., Stewart, D. J., Maroun, J. A., and Nair, R. C. (1990). A randomized phase II study of cisplatin alone versus cisplatin plus disulfiram. Am. J. Clin. Oncol 13, 119–24.
39. Wattenberg, L. W., and Fiala, E. S. (1978). Inhibition of 1,2-dimethyl-hydrazine-induced neoplasia of the large intestine in female CF1 mice by carbon disulfide. J. Natl. Cancer Inst 60, 1515–7.
40. Wride, M. A., Lapchak, P. H., and Sanders, E. J. (1994). Distibution of TNF alpha-like proteins correlates with some regions of programmed cell death in the chick embryo. Int. J. Dev. Biol 38, 673–82.

What is claimed is:

1. A method for inhibiting angiogenesis in an individual which comprises administering to an individual in need therof an amount of disulfiram effective for inhibiting angiogenesis.
2. The method according to claim 1, for the treatment of an angiogenesis-dependent disease selected from the group comprising an ophthalmologic or a neurologic cerebrovascular disorder, a neoplasm, and hypertrophic scars.
3. The method according to claim 2, wherein the ophthalmologic disorder is diabetic retinopathy, corneal graft neovascularization, neovascular glaucoma, trachoma, or retrolental fibroplasis.
4. The method according to claim 2, wherein the neurologic cerebrovascular disorder is arteriovenous malformation.
5. The method according to claim 2, wherein the neoplasm is a leukemia or a solid tumor selected from bladder, brain, breast, cervix, ear, esophagus, hemangioma, kidney, larnyx, liver, lung, ovary, pancreas, prostate, skin, stomach, thyroid, urethra and uterus carcinomas.
6. A method for preventing cell hyperproliferation along or around a medical device which comprises coating the device with disulfiram prior to its insertion into a patient.
7. The method according to claim 5 wherein said medical device is a stent, catheter, cannula, or an electrode.
8. A disulfiram-coated medical device.
9. The disulfiram-coated medical device according to claim 7, wherein the medical device is a stent, catheter, cannula, or an electrode.

* * * * *